United States Patent
Russ et al.

(10) Patent No.: US 10,357,192 B2
(45) Date of Patent: Jul. 23, 2019

(54) VACUUM PRESSURE REGULATORS FOR USE DURING BLOOD COLLECTION

(71) Applicant: Becton, Dickinson and Company, Franklin Lakes, NJ (US)

(72) Inventors: Craig Owen Russ, Wayne, NJ (US); Neville Yu Leng Chia, Singapore (SG); Jamieson W. Crawford, Hagersten (SE); Kenneth James Smith, Flanders, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 391 days.

(21) Appl. No.: 14/889,198

(22) PCT Filed: May 15, 2013

(86) PCT No.: PCT/US2013/041171
§ 371 (c)(1),
(2) Date: Nov. 5, 2015

(87) PCT Pub. No.: WO2014/185904
PCT Pub. Date: Nov. 20, 2014

(65) Prior Publication Data
US 2016/0081606 A1    Mar. 24, 2016

(51) Int. Cl.
| | |
|---|---|
| *A61B 5/15* | (2006.01) |
| *A61M 5/168* | (2006.01) |
| *A61B 5/154* | (2006.01) |
| *A61M 39/24* | (2006.01) |
| *G05D 7/01* | (2006.01) |

(52) U.S. Cl.
CPC .... *A61B 5/150221* (2013.01); *A61B 5/15003* (2013.01); *A61B 5/154* (2013.01);
(Continued)

(58) Field of Classification Search
CPC .......... A61B 5/150221; A61B 5/15003; A61B 5/150099; A61B 5/150389;
(Continued)

(56) References Cited

U.S. PATENT DOCUMENTS

| | | | | |
|---|---|---|---|---|
| 3,395,705 A | * | 8/1968 | Hamilton | A61M 1/0047 604/119 |
| 3,500,864 A | * | 3/1970 | Seiler, Jr. | B64F 1/28 137/220 |

(Continued)

FOREIGN PATENT DOCUMENTS

| | | |
|---|---|---|
| CN | 1517067 A | 8/2004 |
| EP | 0042211 A2 | 12/1981 |

(Continued)

*Primary Examiner* — Daniel L Cerioni
(74) *Attorney, Agent, or Firm* — The Webb Law Firm

(57) ABSTRACT

A regulator for modulation of the flow rate of blood out of a patients blood vessel during blood collection is disclosed. The regulator includes a housing having a housing inlet, a housing outlet, and a wall defining a housing interior. At least a portion of the wall includes a flexible member. A valve is associated with the flexible member and is in communication with the housing interior. The regulator is designed so that upon an application of a differential pressure within the housing interior, the flexible member and/or valve automatically move with respect to either the housing inlet or housing outlet to modulate a flow of blood moving through the housing. A manual over-ride device can be provided to enable a user to over-ride the automatic regulation and manually regulate the flow of blood through the housing.

13 Claims, 19 Drawing Sheets

(52) U.S. Cl.
CPC .... *A61B 5/15074* (2013.01); *A61B 5/150099* (2013.01); *A61B 5/150389* (2013.01); *A61B 5/150503* (2013.01); *A61B 5/150572* (2013.01); *A61B 5/150717* (2013.01); *A61B 5/150732* (2013.01); *A61B 5/150946* (2013.01); *A61M 5/16881* (2013.01); *A61M 39/24* (2013.01); *G05D 7/0113* (2013.01); *A61B 5/150259* (2013.01); *A61M 5/16813* (2013.01); *A61M 2039/246* (2013.01); *A61M 2039/2413* (2013.01); *A61M 2039/2473* (2013.01); *A61M 2039/2486* (2013.01)

(58) Field of Classification Search
CPC ........ A61B 5/150503; A61B 5/150572; A61B 5/150717; A61B 5/150732; A61B 5/15074; A61B 5/150946; A61B 5/154; A61M 5/16881; A61M 39/24; G05D 7/0113
USPC .......................................................... 600/578
See application file for complete search history.

(56) References Cited

U.S. PATENT DOCUMENTS

| | | | |
|---|---|---|---|
| 3,848,579 A | 11/1974 | Villa-Real | |
| 4,340,068 A | 7/1982 | Kaufman | |
| 5,453,097 A * | 9/1995 | Paradis | A61M 39/24 137/849 |
| 5,807,358 A * | 9/1998 | Herweck | A61M 1/0013 604/320 |
| 6,749,592 B2 * | 6/2004 | Lord | A61M 1/0031 604/317 |
| 2003/0216687 A1 * | 11/2003 | Hwang | A61M 5/3275 604/110 |
| 2004/0143226 A1 | 7/2004 | Marsden | |
| 2005/0075612 A1 | 4/2005 | Lee et al. | |
| 2006/0009714 A1 | 1/2006 | Higaki et al. | |
| 2008/0066810 A1 | 3/2008 | Barak | |
| 2008/0086085 A1 | 4/2008 | Brown | |
| 2012/0180875 A1 | 7/2012 | Keller et al. | |
| 2013/0197621 A1 | 8/2013 | Ryan et al. | |
| 2013/0303987 A1 | 11/2013 | Esnouf | |

FOREIGN PATENT DOCUMENTS

| | | |
|---|---|---|
| EP | 1614384 A2 | 1/2006 |
| EP | 1897585 A1 | 3/2008 |
| WO | 0037128 A1 | 6/2000 |
| WO | 0211613 A2 | 2/2002 |
| WO | 2012021406 A2 | 2/2012 |
| WO | 2012061869 A1 | 5/2012 |

* cited by examiner

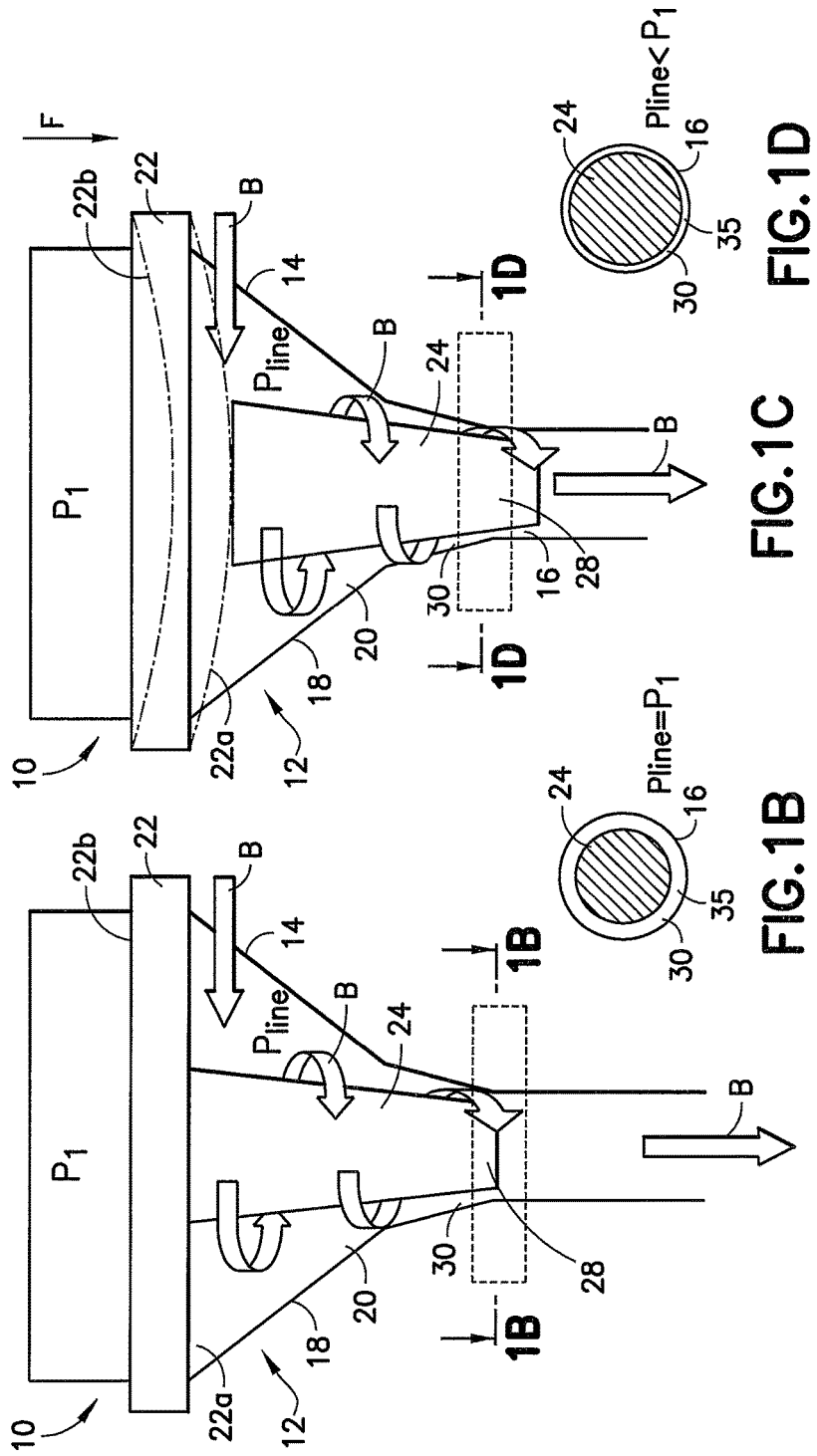

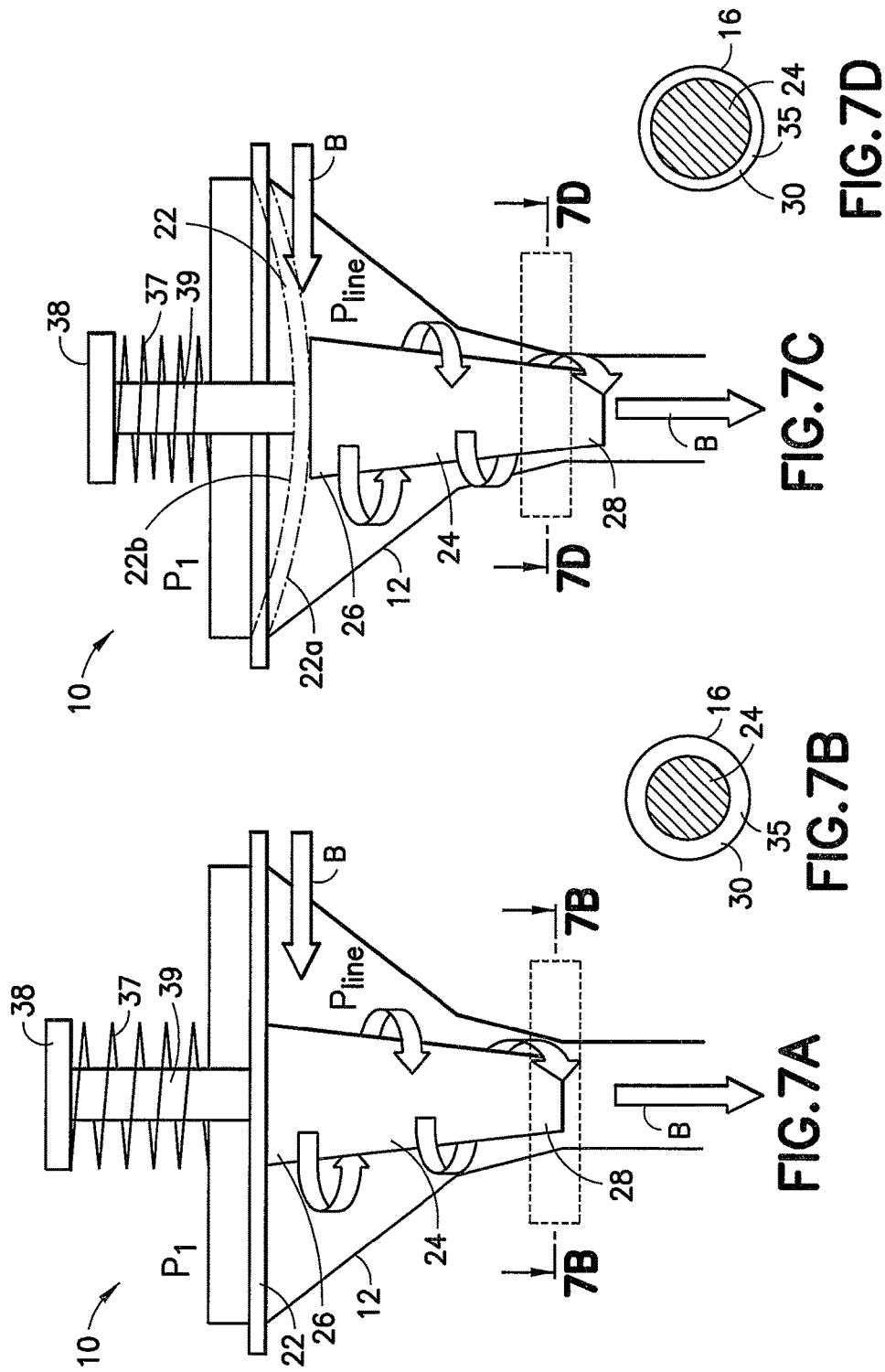

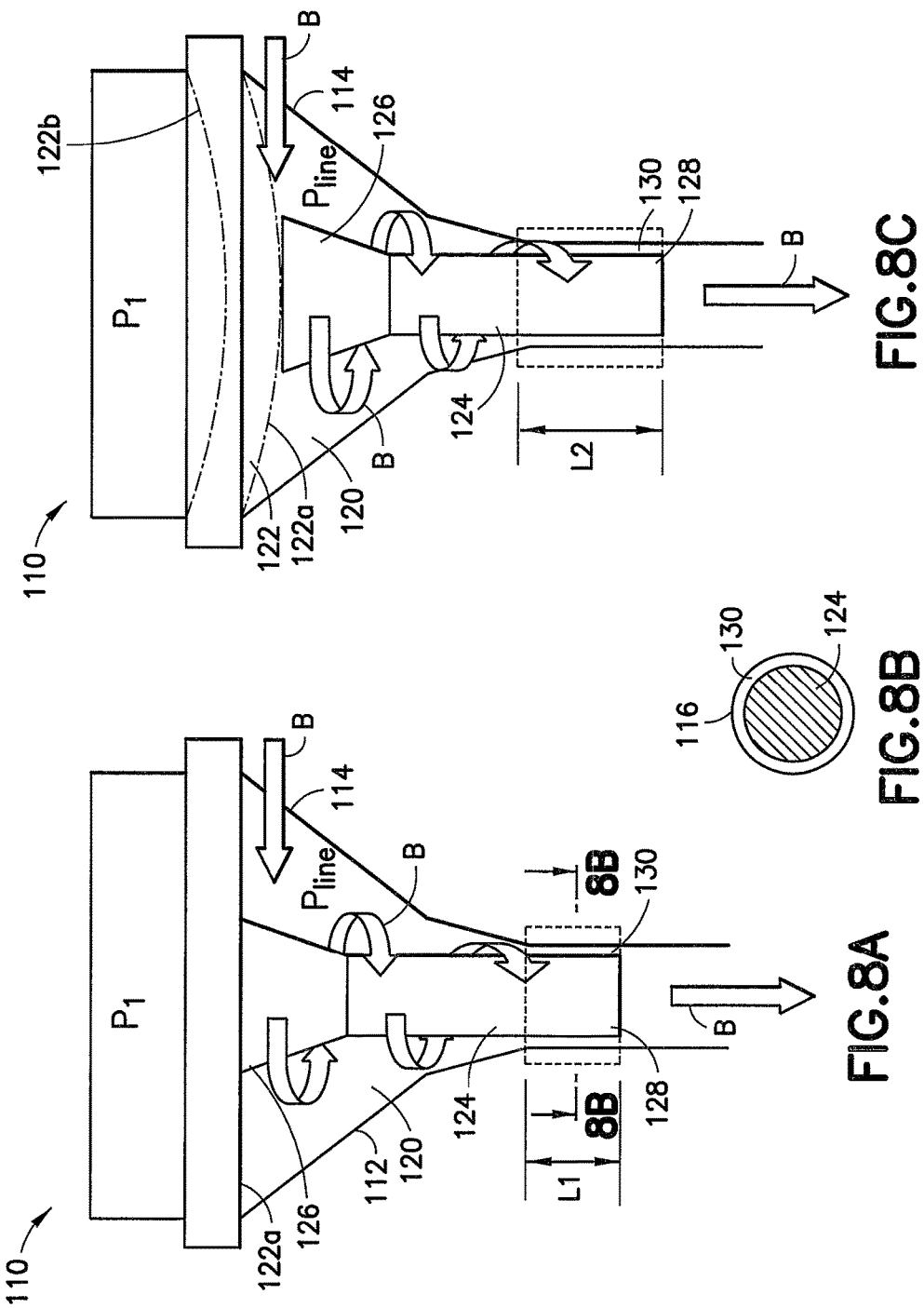

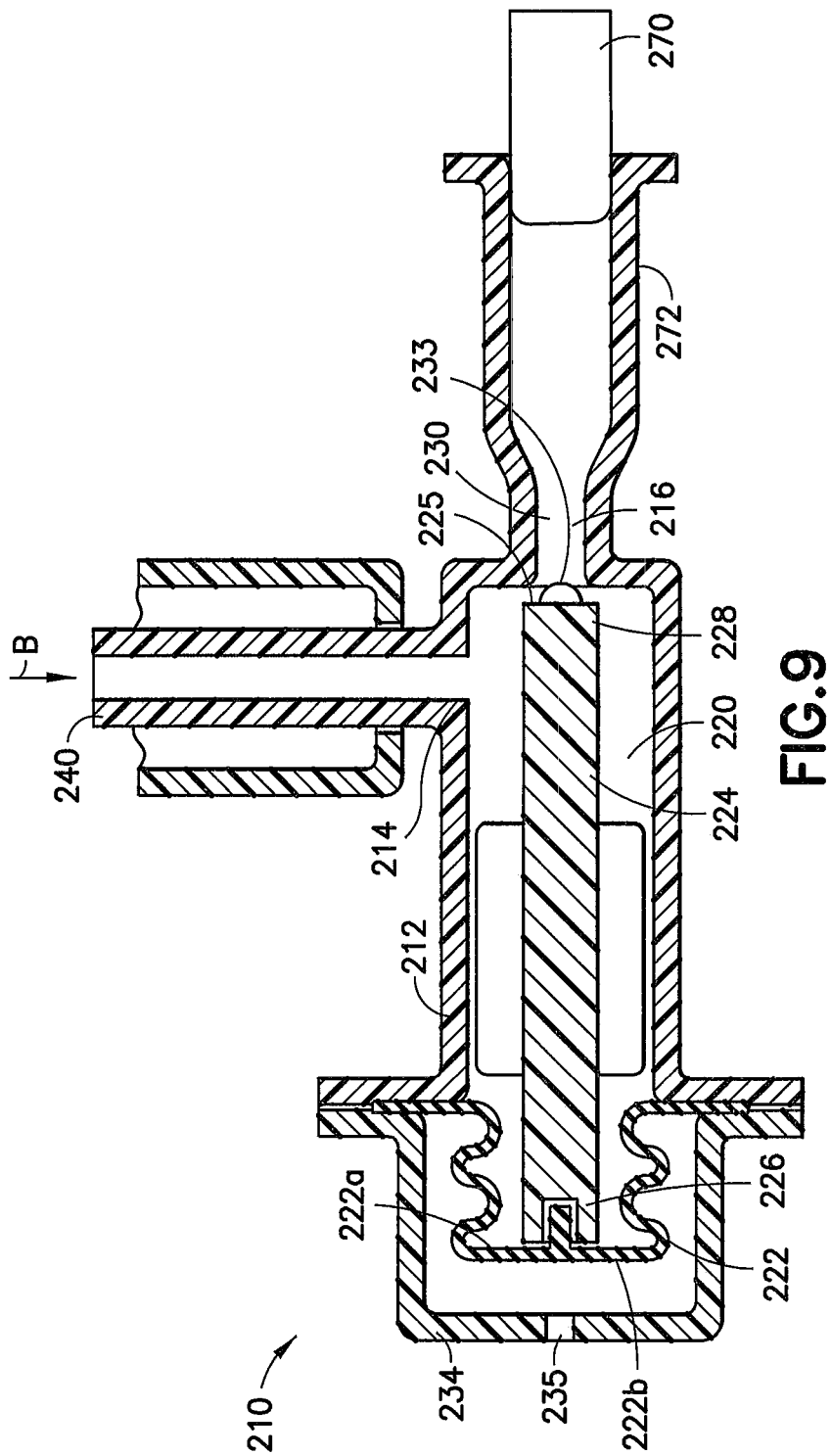

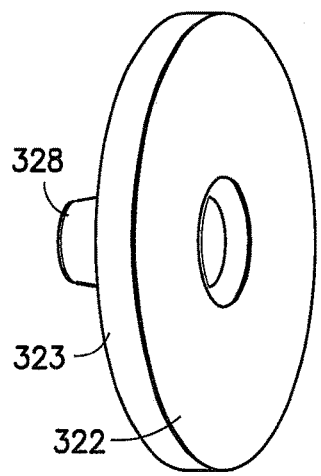
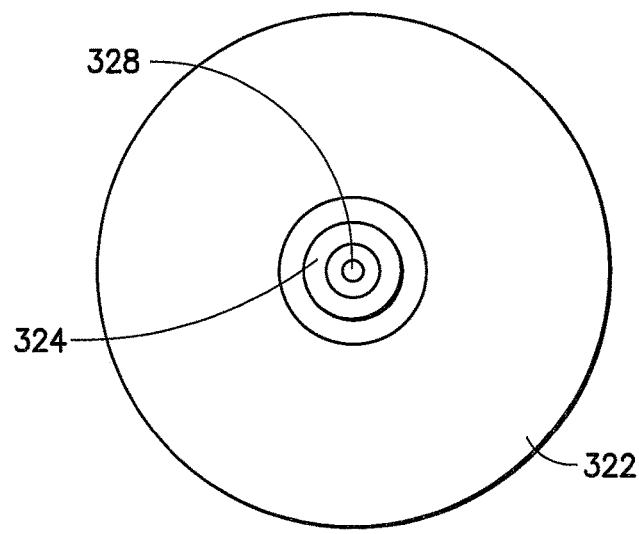
FIG.15A
FIG.15B
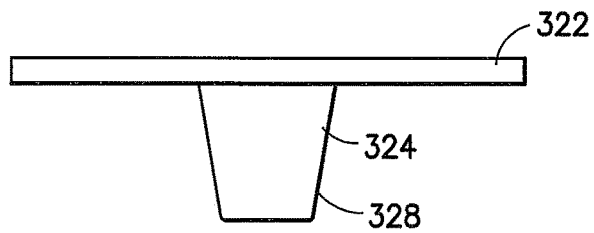
FIG.15C
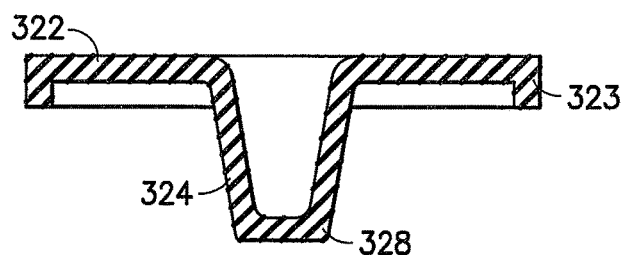
FIG.15D

VACUUM PRESSURE REGULATORS FOR USE DURING BLOOD COLLECTION

CROSS-REFERENCE TO RELATED APPLICATIONS

This application is the United States national phase of International Application No. PCT/US2013/041171 filed May 15, 2013 the disclosure of which is hereby incorporated in its entirety by reference.

BACKGROUND OF THE INVENTION

Field of the Invention

The present invention relates to a regulator for flow modulation to prevent the collapse of a blood vessel during blood collection and, more particularly, to a variable flow resistor that acts to slow down the initial flow rate of blood into an evacuated blood collection device. The present invention also minimizes the initial spike in flow rate caused by vacuum pressure and slows down the overall blood collection time to avoid rapid depletion of resident blood within the vessel.

Description of Related Art

Phlebotomy procedures are often carried out using a blood collection device or intravenous (IV) infusion device. A typical blood collection or (IV) infusion device includes a needle assembly having a cannula that includes a proximal end, a pointed distal end, and a lumen extending therebetween. The needle assembly also includes a hub with a proximal end, a distal end, and a passage extending between the ends. The proximal end of the cannula is mounted in the passage of the hub so that the lumen of the cannula communicates with the passage through the hub. A shield may be provided for shielding the distal end of the cannula after use. The blood collection set may also include a wing member that projects transversely from the hub or from the shield. The wings of the wing member can be folded with respect to each other to define a handle that facilitates manipulation of the needle assembly. The wings then can be rotated apart and held against the skin of the patient.

Typical blood collection devices may also include a length of flexible plastic tubing. The tubing has a distal end that is connected to the proximal end of the hub and communicates with the lumen of the needle cannula. The end of the plastic tube remote from the needle cannula may include a fixture for connecting the needle cannula to a blood collection tube or other receptacle. Phlebotomy procedures often employ evacuated tubes, such as the VACUTAINER® brand of evacuated tubes commercially available from Becton, Dickinson and Company. Evacuated tubes often are used with a tube holder that has a proximal end, a distal end, and a tubular side wall extending between the ends. The proximal end of the holder is generally open and configured for slidably receiving the evacuated tube. The distal end of the holder typically includes an end wall with a mounting aperture. The tube holder may be used with a non-patient needle assembly that has a non-patient hub configured for cooperation with the mounting aperture of the holder. The non-patient needle assembly further includes a non-patient cannula extending proximally from the hub and into the tube holder.

The blood collection set may be used by mounting the fitting at the proximal end of the flexible plastic tubing to the distal end of the hub of the non-patient needle assembly. The pointed distal end of the cannula is urged into a targeted blood vessel, such as a vein, by gripping of the wings of the wing member for manipulation of the cannula. The wings may then be folded into engagement with the skin of the patient and may be taped in position. An evacuated tube is urged into the open proximal end of the blood collection tube holder so that the proximal end of the non-patient needle pierces the stopper of the evacuated tube. As a result, the blood vessel of the patient is placed in communication with the interior of the evacuated tube, and the pressure differential between the blood vessel and the evacuated tube will generate a flow of blood through the cannula, the hub, the flexible tubing, the non-patient hub, the non-patient needle, and into the evacuated tube.

Collapse of the patient's blood vessel during blood collection can occur as a result of a pressure differential created by the connection of the evacuated tube to the non-patient needle cannula. This collapse can occur as a result of the blood being removed too quickly from the patient's blood vessel due to the vacuum draw of the evacuated tube. When a standard evacuated tube is connected to a blood collection set, there is an instantaneous introduction of a sharp vacuum pressure applied to the patient's blood vessel. This strong vacuum results in a spiked flow rate of blood out of the patient's blood vessel. This sharp outflow of blood can lead to the vessel wall collapsing against the bevel of the distal end of the patient cannula, resulting in flow stoppage.

Accordingly, a need exists for a vacuum pressure regulator which minimizes the incidence of vessel or vein collapse.

SUMMARY OF THE INVENTION

The vacuum pressure regulator of the present invention minimizes vessel collapse by controlling the flow rate of the blood out of the patient's blood vessel. The present invention slows down the initial flow rate of blood into an evacuated tube to avoid the initial pressure spike.

In accordance with an embodiment of the present invention, a regulator for flow modulation during blood collection to prevent the collapse of a patient's blood vessel includes a housing having a housing inlet, a housing outlet, and a wall defining a housing interior, at least a portion of the wall comprising a flexible member and a valve associated with the flexible member. The valve is in communication with the housing interior and is configured so that upon an application of a differential pressure within the housing interior, the flexible member and valve automatically move with respect to either the housing inlet or housing outlet to modulate a flow of blood moving through the housing.

In certain configurations, the valve can be movable with respect to the housing outlet to vary the geometry of an orifice of the housing outlet. It can be appreciated that the valve can cooperate with either the housing inlet or outlet to vary the flow of blood and fluid throughout the housing. The flexible member can be a membrane formed from any type of flexible, resilient material selected, such as thermoplastic elastomers (TPE), silicone, and the like. The flexible member can have spring-like properties which enable it to return to its at-rest position and is anchored about its perimeter to the wall of the housing. The flexible member can have a first face adjacent the housing interior and a second face toward the atmosphere. The flexible member can act as a barrier between the blood flowing through the housing and the atmosphere. The valve can be secured to the first face of the flexible member. The housing inlet can be associated with a blood source, such as a patient's vein or artery, and the housing outlet can be associated with a vacuum source, such as a vacuum blood collection tube, and the pressure differential can be initiated by the application of vacuum from the vacuum blood collection tube to the housing outlet. The application of a vacuum to the housing outlet from the vacuum blood collection tube during an initial blood collection process causes a pressure difference across the membrane to force at least one of the flexible member and valve into an orifice of at least one of the housing inlet or the housing outlet to provide flow resistance to the blood flowing through the housing outlet and to slow the flow rate of the blood through the housing inlet and the housing itself during the initial stages of blood collection. As the blood collection tube begins to fill, the force applied from the vacuum decreases and equalization of the vacuum pressure within the housing occurs. This equalization of pressure within the housing interior and with the atmosphere causes the flexible member and valve to withdraw from the orifice of the housing outlet and to allow the blood to flow at an unrestricted rate through the housing and exit the housing outlet, thereby modulating the flow of blood through the regulator.

The regulator is configured for integration with a blood collection wingset. In certain configurations, the wingset includes a hub, tubing, and a blood collection holder and the regulator can be directly associated with the hub, positioned in-line with the tubing, or can be directly associated with the collection holder.

The flexible member of the regulator can be a resilient membrane having spring properties. The resilient membrane can be anchored about its perimeter to the wall of the housing and the valve can be secured to the membrane. The regulator can include a thumb pad associated with the flexible member to enable the user to over-ride the automatic regulation of blood flow and to manually regulate the flow of blood through the housing. Also, a separate spring may be associated with the atmospheric side of the flexible member.

According to one configuration, the valve can be a needle valve. According to another configuration, the valve can be a poppet valve having a flat shut off. According to yet another configuration, the valve can comprise a concentric annulus having an inner stem connected to the flexible member and wherein the application of vacuum within the housing causes the flexible member to be drawn into the housing interior to lengthen the concentric annulus. This results in an increase of fluid resistance of blood flow through the housing inlet or housing outlet. As the vacuum pressure dissipates, the pressure in the housing interior raises the flexible member with respect to the housing interior to decrease the length of the concentric annulus with respect to the housing inlet or housing outlet. This results in a decrease of fluid resistance of blood flow through the housing inlet. According to still another configuration, the housing inlet or housing outlet can include a seal ring having a small flow channel and the valve can comprise the flexible member itself which is drawn toward the seal ring to cooperate with the seal ring and small flow channel to reduce or restrict the flow of blood through the small flow channel upon the application of a differential pressure within the housing interior. The flexible member can comprise at least one spring element that causes the membrane to bias toward an unflexed position away from the seal ring upon an equalization of pressure within the housing interior.

In accordance with another embodiment of the present invention, a method of regulating flow of blood through a wingset during blood collection includes associating a vacuum pressure regulator with the wingset, inserting a patient end of a cannula of the wingset into a patient's blood vessel, and connecting a non-patient end of a cannula of said wingset with a vacuum blood collection tube. The vacuum pressure regulator includes a housing having a housing inlet, a housing outlet, and a wall defining a housing interior. At least a portion of the wall comprises a flexible member and a valve is associated with the flexible member. The valve extends into the housing interior. Upon an application of a vacuum pressure within the housing interior caused by the connection of the blood collection tube, the flexible member and valve are automatically moved toward either the housing inlet or housing outlet to restrict an orifice opening of the housing inlet or housing inlet and to modulate the flow of blood moving through the housing.

The wingset can include a hub, tubing, and a blood collection holder. The vacuum pressure regulator can be directly associated with the hub, positioned in-line with the tubing, or directly associated with the blood collection holder. The method can also include associating a thumb pad with the flexible member to enable the user to over-ride the automatic regulation of blood flow and to manually regulate the flow of blood through the housing. According to various configurations, the valve can comprise one of a needle valve, a poppet valve having a flat shut-off, or a concentric annulus. According to another configuration, the method can further include associating a seal ring having a small flow channel with either the housing inlet or the housing outlet of the regulator and the valve can comprise the flexible member that is drawn toward the seal ring to cooperate with the seal ring and small flow channel to reduce or restrict the flow of blood through the small flow channel upon the application of the vacuum pressure within the housing interior. The method can also include associating a spring with an atmospheric side of the flexible member.

In accordance with another embodiment of the present invention, a wingset including a regulator for flow modulation during blood collection includes a first cannula having a patient end, a second cannula having a non-patient end, a hub and tubing positioned between the first and second cannulae, and a tube holder associated with said second cannula. The tube holder is configured for receiving a blood collection tube of the type that includes a seal for containing a vacuum pressure therein sufficient for drawing blood into the tube. A regulator is associated with either the hub, tubing, or tube holder. The regulator includes a housing having a housing inlet, a housing outlet, and a wall defining a housing interior. At least a portion of the wall comprises a flexible member and a valve is associated with the flexible member. The valve extends into the housing interior. Upon insertion of the blood collection tube within the tube holder and piercing of the seal of the blood collection tube, the vacuum contained within the tube causes an application of a differential pressure, i.e., a vacuum pressure, within the housing interior, resulting in the automatic movement of the flexible member and valve with respect to either the housing inlet or housing outlet to modulate a flow of blood moving through the housing.

The wingset can include a thumb pad associated with the flexible member to enable the user to over-ride the automatic regulation of blood flow and to manually regulate the flow of blood through the housing. According to various configurations, the valve can comprise a needle valve, a poppet valve having a flat shut-off, or a concentric annulus. According to another configuration, the regulator includes a seal ring having a small flow channel associated with either the housing inlet or the housing outlet and the valve itself can comprise the flexible member. Upon the application of the differential pressure within the housing interior, the flexible member is drawn toward the seal ring to cooperate with the seal ring and small flow channel to reduce or restrict the flow of blood through the small flow channel and thus to regulate the flow of blood through the housing. A spring can also be associated with an atmospheric side of the flexible member.

These and other features and characteristics of the present invention, as well as the methods of operation and functions of the related elements of structures, and the combination of parts and economies of manufacture, will become more apparent upon consideration of the following description with reference to the accompanying drawings, all of which form a part of this specification, wherein like reference numerals designate corresponding parts in the various figures.

BRIEF DESCRIPTION OF THE DRAWINGS

FIG. 1A is a schematic cross-sectional front view of the pressure regulator of FIG. 1 wherein the pressure in the fluid transport line is equal to atmospheric pressure allowing for unrestricted fluid flow in accordance with an embodiment of the present invention.

FIG. 1B is a partial cross-sectional view of the regulator of FIG. 1A taken along line 1B-1B in accordance with an embodiment of the present invention.

FIG. 1C is a schematic cross-sectional front view of the pressure regulator of FIG. 1 wherein the pressure in the fluid transport line is less than atmospheric pressure resulting in restricted fluid flow in accordance with an embodiment of the present invention.

FIG. 1D is a partial cross-sectional view of the regulator of FIG. 1C taken along line 1D-1D in accordance with an embodiment of the present invention.

FIG. 7A is a schematic cross-sectional front view of a pressure regulator wherein the pressure in the fluid transport line is equal to atmospheric pressure allowing for unrestricted fluid flow in accordance with an embodiment of the present invention.

FIG. 7B is a partial cross-sectional view of the regulator of FIG. 7A taken along line 7B-7B in accordance with an embodiment of the present invention.

FIG. 7C is a schematic cross-sectional front view of the pressure regulator of FIG. 7A wherein the pressure in the fluid transport line is less than atmospheric pressure resulting in restricted fluid flow in accordance with an embodiment of the present invention.

FIG. 7D is a partial cross-sectional view of the regulator of FIG. 7C taken along line 7D-7D in accordance with an embodiment of the present invention.

FIG. 8A is a schematic cross-sectional front view of a pressure regulator wherein the pressure in the fluid transport line is equal to atmospheric pressure allowing for unrestricted fluid flow in accordance with an embodiment of the present invention.

FIG. 8B is a partial cross-sectional view of the regulator of FIG. 8A taken along 8B-8B in accordance with an embodiment of the present invention.

FIG. 8C is a schematic cross-sectional front view of the pressure regulator of FIG. 8A wherein the pressure in the fluid transport line is less than atmospheric pressure resulting in restricted fluid flow in accordance with an embodiment of the present invention.

FIG. 9 is a cross-sectional view of a pressure regulator in accordance with another embodiment of the present invention.

FIG. 15A is a side perspective view of the diaphragm used in the pressure regulator of FIGS. 10A and 10B in accordance with an embodiment of the present invention.

FIG. 15B is a top view of the diaphragm used in the pressure regulator of FIGS. 10A and 10B in accordance with an embodiment of the present invention.

FIG. 15C is a side elevation view of the diaphragm used in the pressure regulator of FIGS. 10A and 10B in accordance with an embodiment of the present invention.

FIG. 15D is a cross-sectional side elevation view of the diaphragm of FIG. 15C in accordance with an embodiment of the present invention.

BRIEF DESCRIPTION OF THE INVENTION

Figure 1:
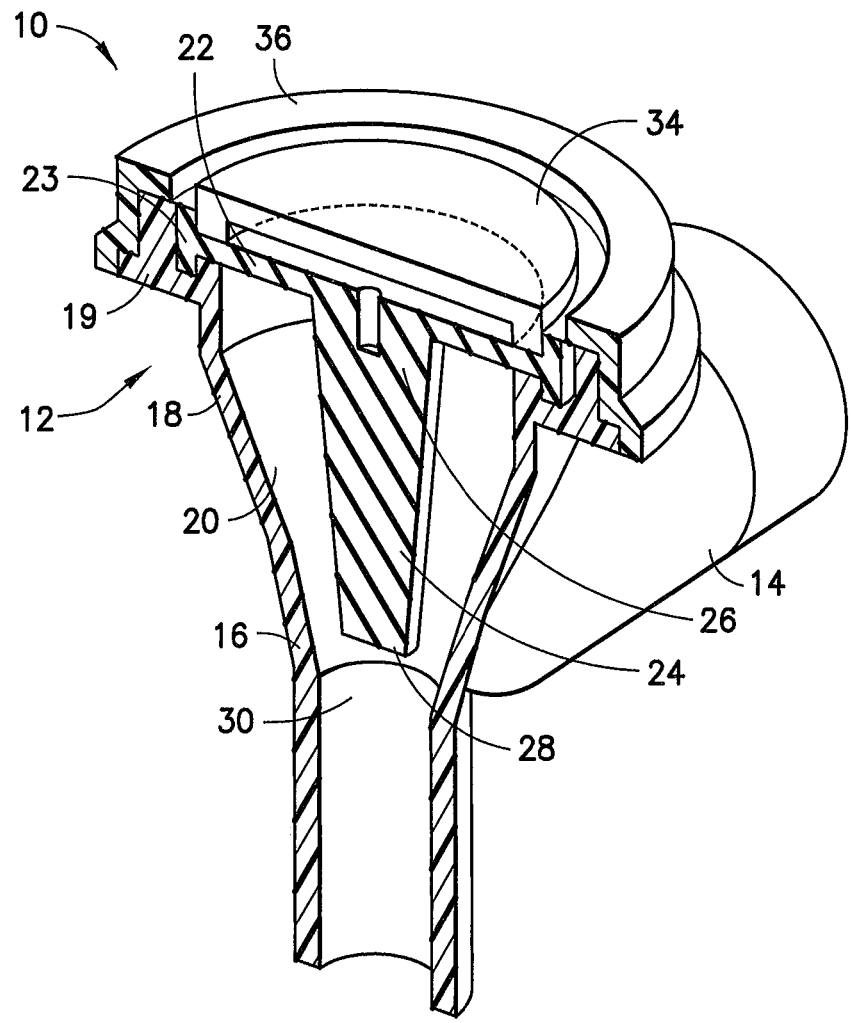
FIG. 1 is a cross-sectional perspective view of a pressure regulator in accordance with an embodiment of the present invention.

For purposes of the description hereinafter, the terms "upper", "lower", "right", "left", "vertical"; "horizontal", "top", "bottom", "lateral", "longitudinal", and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIG. 1, which shows a pressure regulator, generally indicated as 10, for flow modulation during blood collection to prevent the collapse of a patient's blood vessel. The regulator comprises a housing, generally indicated as 12, having a housing inlet 14, a housing outlet 16, and a wall 18 defining a housing interior 20. The housing outlet 16 includes an orifice 30. The regulator 10 further includes a flexible member 22 and a valve 24 having a first end 26 associated with the flexible member 22. The valve 24 extends into the housing interior 20 and is configured at a second end 28 to cooperate with the orifice 30. It can be appreciated that the second end 28 of the valve 24 can cooperate with the orifice 30 located at either the housing inlet 14 or the housing outlet 16, however, for the purposes of clarity with respect to the drawings, the second end 28 of the valve 24 is shown cooperating with the housing outlet 16. Accordingly, upon an application of a differential pressure within the housing interior 20, the flexible member 22 and valve 24 automatically move with respect to the housing outlet 16 to reduce the orifice 30 of the housing outlet 16 which modulates or restricts a flow of fluid, such as blood, moving through the housing outlet 16 and consequently through the housing interior 20.

Figure 3:
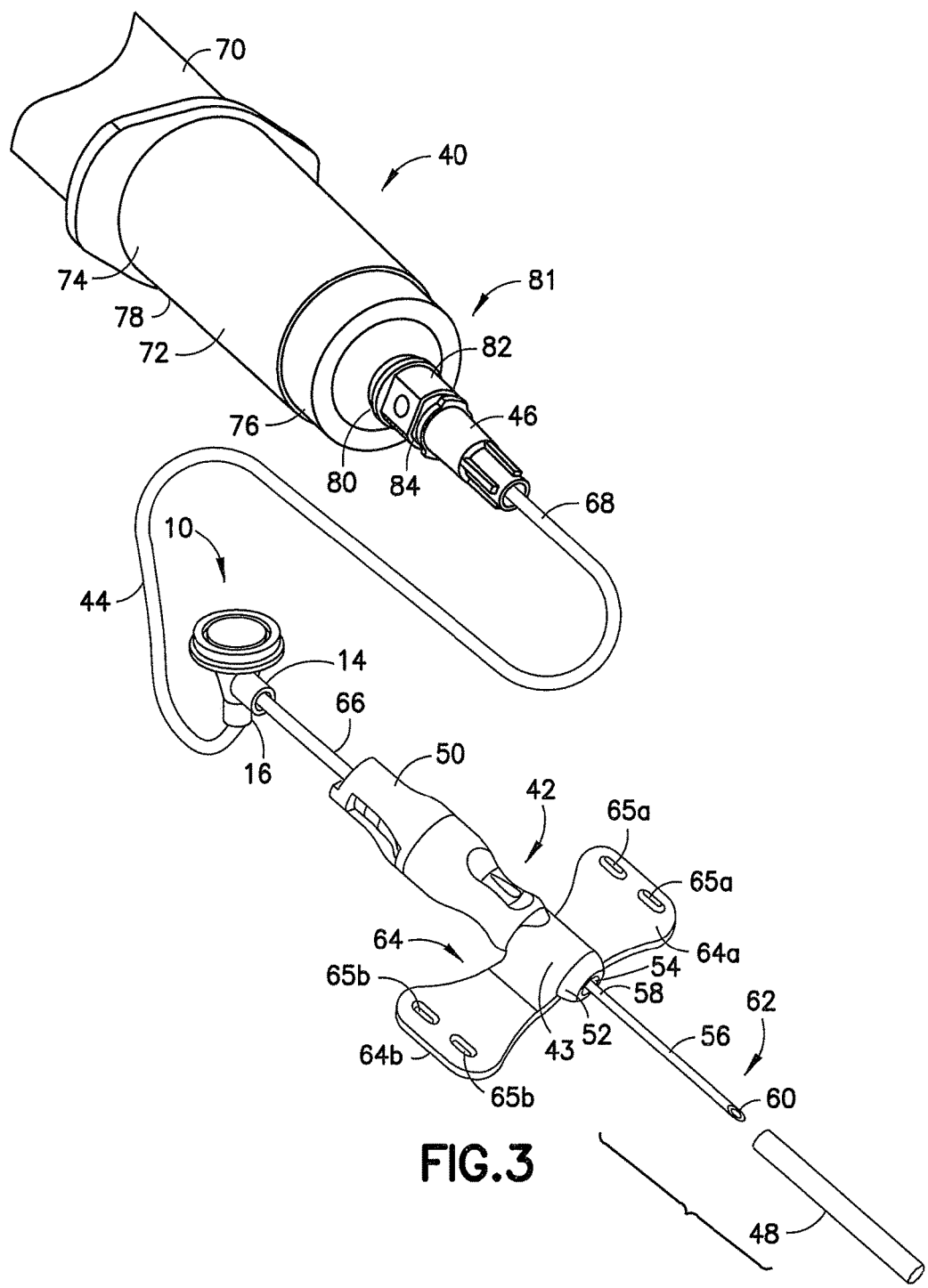
FIG. 3 is a perspective view of a blood collection set including the regulator of FIG. 1 in accordance with an embodiment of the present invention.
Figures 4, 5:
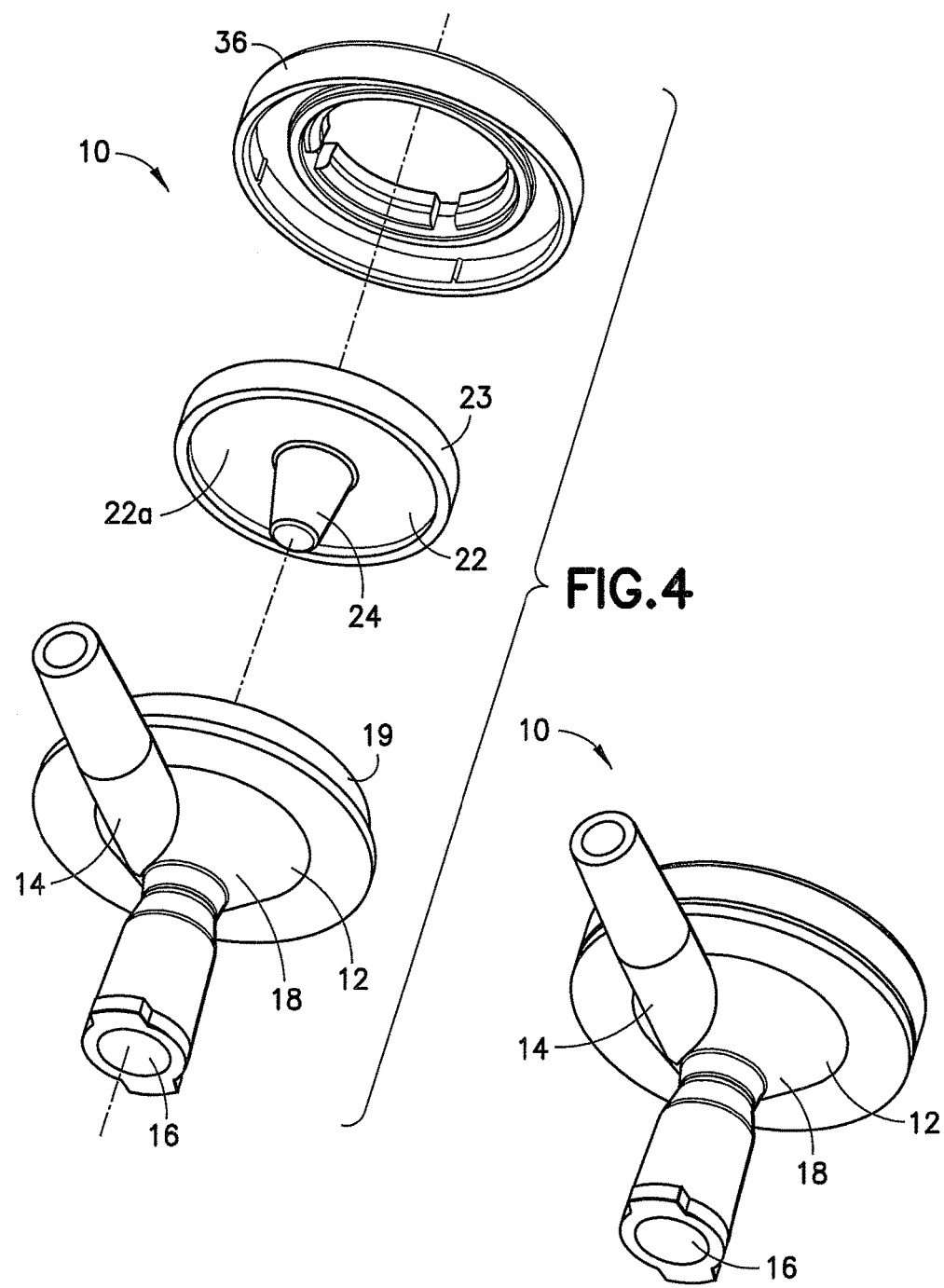
FIG. 4 is an exploded perspective view of the vacuum pressure regulator of FIG. 1 in accordance with an embodiment of the present invention.
FIG. 5 is a bottom perspective view of the vacuum pressure regulator of FIG. 4 in accordance with an embodiment of the present invention.
Figure 5A:
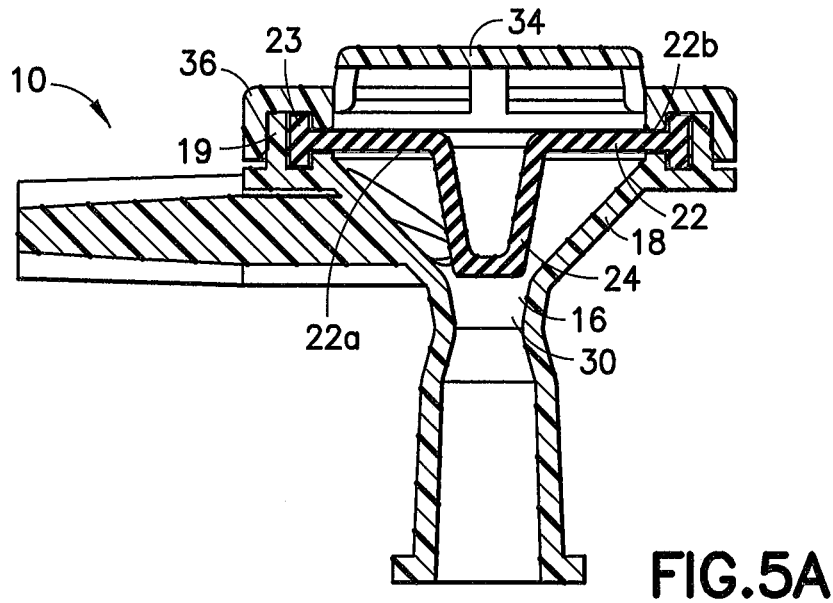
FIG. 5A is a left cross-sectional view of the vacuum pressure regulator of FIG. 5 taken along line 5A-5A of FIG. 5B in accordance with an embodiment of the present invention.
Figure 5B:
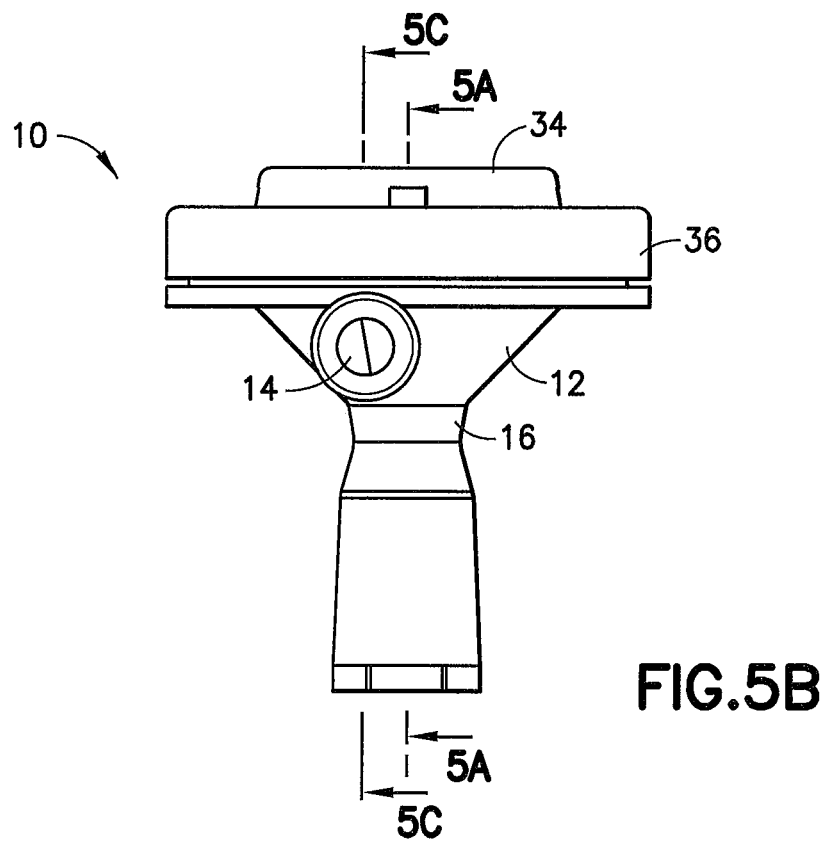
FIG. 5B is a side elevation view of the vacuum pressure regulator of FIG. 5 in accordance with an embodiment of the present invention.
Figure 5C:
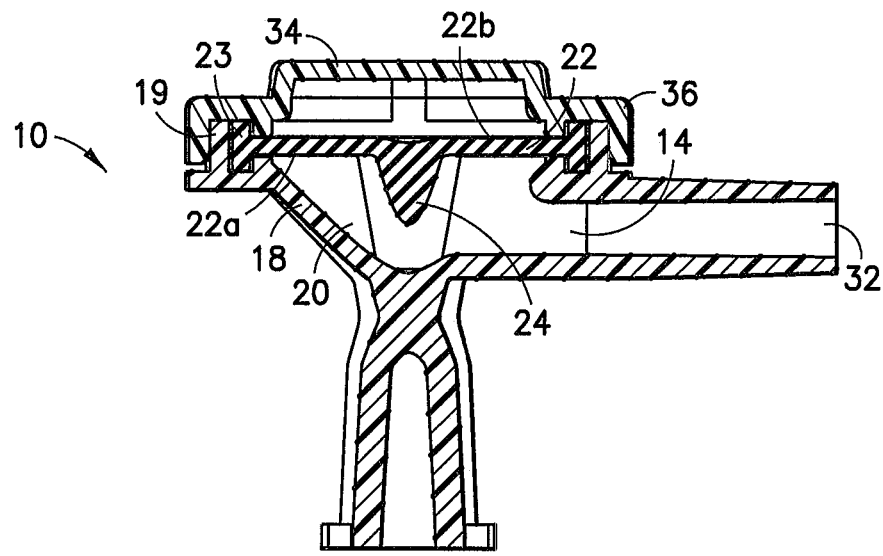
FIG. 5C is a right cross-sectional view of the vacuum pressure regulator of FIG. 5 taken along line 5C-5C of FIG. 5B in accordance with an embodiment of the present invention.
Figure 5D:
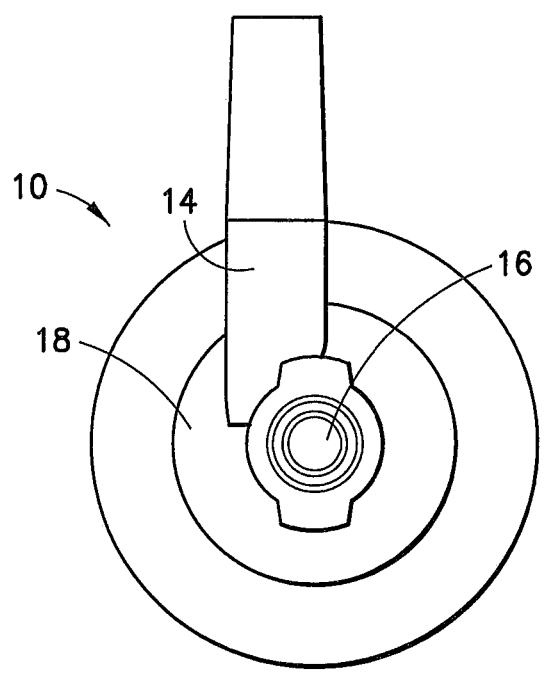
FIG. 5D is a bottom view of the vacuum pressure regulator of FIG. 5 in accordance with an embodiment of the present invention.

Reference is now made to FIG. 3 which shows an example of one type of blood collection device, generally indicated as 40, with which the pressure regulator 10 can be used. The blood collection device 40 can be in the form of a wingset and include a needle device, generally indicated as 42, including a hub 43, which can include a shielding device (not shown), a flexible tube 44 extending from the needle device 42, and a fixture 46 mounted to the tube 44. An optional packaging cover 48 can be removably mounted to the needle device 42 opposite tube 44, such as through frictional engagement or any other well known mounting arrangement. The hub 43 includes a proximal end 50, a distal end 52, and a passage 54 extending between the ends. A needle cannula 56 is provided which includes a first or proximal end 58 and an opposing second or distal end 60 and a lumen 62 extending through the cannula 56. The proximal end 58 of the cannula 56 is mounted in the passage 54 of the hub 43 so that the lumen 62 through the cannula 56 communicates with the passage 54 through the hub 43.

The blood collection device 40 may also include a wingset, generally indicated as 64, which projects transversely from the hub 43 or from the shield (not shown). Wing members 64a, 64b of the wingset 64 can be folded into face-to-face relationship with one another and secured, such as with male and female interlocking members 65a, 65b, to define a handle that facilitates manipulation of the needle device/hub 42, 43. The wing members 64a, 64b can be unlocked and then rotated away from one another and held or secured, such as by surgical tape, against the skin of the patient. As discussed above, the blood collection device 40 also includes a length of flexible plastic tubing 44. The tubing 44 has a distal end 66 that is connected to the proximal end 50 of the hub 43 and communicates with the lumen 62 of the needle cannula 56. A proximal end 68 of the tubing 44 may include fixture 46 for connecting the needle cannula 56 to a blood collection tube or other receptacle 70. A holder 72 may be provided to hold the tube or other receptacle 70. The specific construction of the fixture 46 will depend upon the characteristics of the receptacle 70 to which the fixture 46 is to be connected.

One type of receptacle 70 that is often used with blood collection devices is an evacuated tube. Evacuated tubes 70 often are used with a tube holder 72 that has a proximal end 74, a distal end 76, and a tubular side wall 78 extending between the ends 74, 76. The proximal end 74 of the holder 72 is widely open and is configured for slidably receiving the evacuated tube 70. The distal end 76 of the holder 72 typically includes an end wall with a mounting aperture 80. The tube holder 72 may be used with a non-patient needle assembly, generally indicated as 81, that has a non-patient hub 82 configured for cooperation with the mounting aperture 80 of the holder 72. The non-patient needle assembly 81 further includes a non-patient cannula (not shown) extending proximally from the hub 82 and into the tube holder 72.

The blood collection device 40 may be used by mounting the fixture 46 at the proximal end 68 of the flexible plastic tubing 44 to a distal end 84 of the hub 82 of the non-patient needle assembly 81. The pointed distal end 60 of the cannula 56 is urged into a targeted blood vessel, such as a vein, by gripping of the wing members 64a, 64b of the wingset 64 for manipulation of the cannula 56. The wing members 64a, 64b may then be folded into engagement with the skin of the patient and may be taped in position. An evacuated tube 70 is urged into the open proximal end 74 of the blood collection tube holder 72 so that the proximal end of the non-patient needle (not shown) pierces the stopper (not shown) of the evacuated tube 70. As a result, the blood vessel of the patient is placed in communication with the interior of the evacuated tube 70, and the pressure differential between the blood vessel and the evacuated tube 70 will generate a flow of blood through the cannula 56, the passage 54 of the hub 43, the flexible tubing 44, the non-patient hub 82, the non-patient needle (not shown), and into the evacuated tube 70.

Collapse of the patient's blood vessel during blood collection can occur as a result of the pressure differential created by the connection of the evacuated tube 70 to the non-patient needle cannula. This collapse can occur as a result of the blood being removed too quickly from the patient's blood vessel. Physiological conditions such as the elasticity of the vessel wall can also contribute to this problem. With a standard evacuated tube 70, there is an instantaneous introduction of a sharp vacuum pressure when the evacuated tube 70 is attached to the non-patient end of the blood collection device 40. This sharp vacuum pull results in an initially high flow rate of blood out of the patient's blood vessel. This sharp outflow of blood coupled with the high elasticity of a patient's vessel can lead to the vessel wall collapsing onto the bevel of the distal end 60 of the patient cannula 56 resulting in flow stoppage.

With continuing reference to FIG. 1 and with reference to FIGS. 1A, 1B, 2A, 2B, 4, and 5A-5D, the pressure regulator 10 of the present invention is associated with the blood collection device 40 to modulate the flow of fluid, i.e., both the flow of vacuum pressure and the flow of blood, during blood collection to prevent the collapse of a patient's blood vessel. Specifically, the pressure regulator 10 controls the level of vacuum pull or vacuum pressure moving through the blood collection device 40 so as to minimize the effect of the initial sharp pull of vacuum caused by the connection of the vacuum tube 70 to the non-patient cannula and to slow down the removal of the blood from the patient's blood vessel. This control of fluid flow prevents collapse of the patient's blood vessel. The pressure regulator 10 includes the housing 12 having the wall 18 defining a housing interior 20 wherein a portion of the wall includes the flexible member or diaphragm 22. A valve 24 is associated with the flexible member 22. The valve 24 extends into the housing interior 20 and is configured so that upon an application of a differential pressure within the housing interior 20, the flexible member 22 and valve 24 automatically move with respect to the housing outlet 16 to reduce the orifice 30 of the housing outlet 16, as shown by arrow "M" in FIG. 2B, and modulate or restrict a flow of blood, as depicted by arrow "B", shown in FIGS. 1A, 1C, 2A, and 2B, moving through the housing outlet 16 and consequently through the housing 12.

Figure 2A:
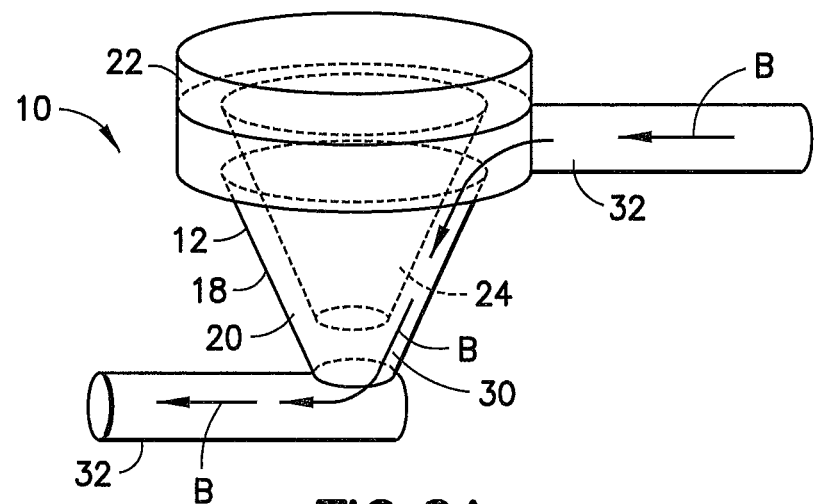
FIG. 2A is a perspective view of a pressure regulator wherein the pressure in the fluid transport line is equal to atmospheric pressure allowing for unrestricted fluid flow in accordance with an embodiment of the present invention.
Figure 2B:
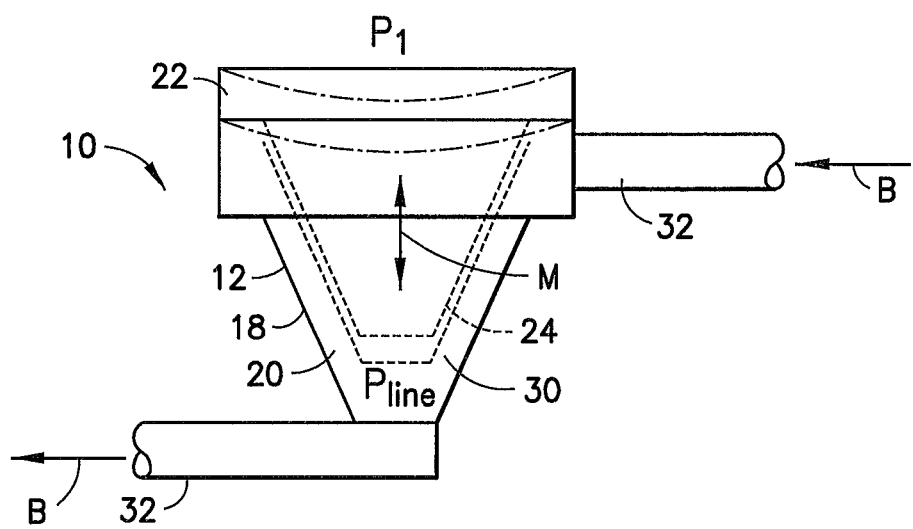
FIG. 2B is a schematic cross-sectional front view of the pressure regulator of FIG. 2A wherein the pressure in the fluid transport line is less than atmospheric pressure resulting in restricted fluid flow in accordance with an embodiment of the present invention.
Figure 6A:
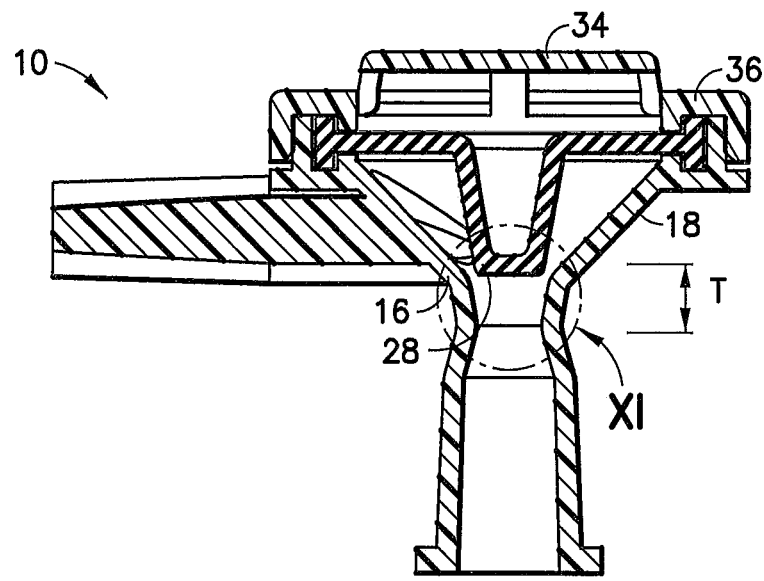
FIG. 6A is a left cross-sectional view of the vacuum pressure regulator of FIG. 5 showing the location of the valve of the regulator prior to its movement to restrict the flow of fluid therethrough in accordance with an embodiment of the present invention.
Figure 6B:
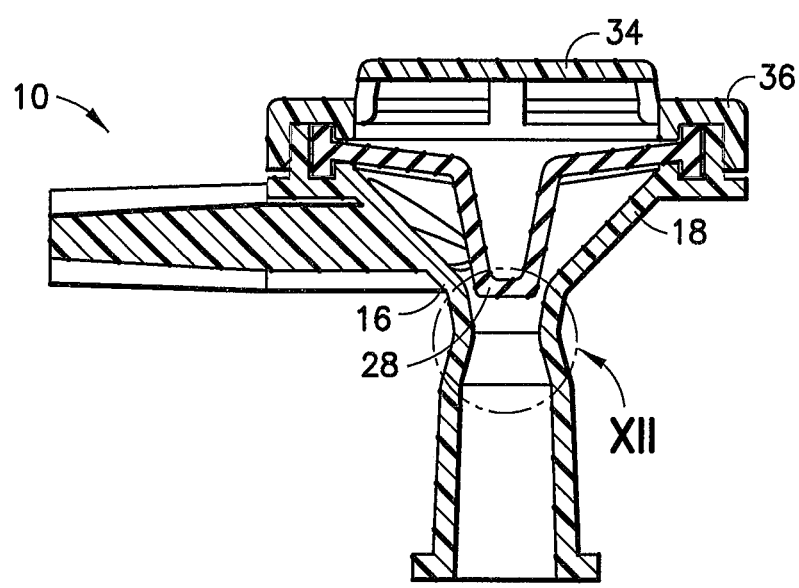
FIG. 6B is a left cross-sectional view of the vacuum pressure regulator of FIG. 5 showing movement of the valve of the regulator to restrict the flow of fluid therethrough in accordance with an embodiment of the present invention.
Figure 6C:
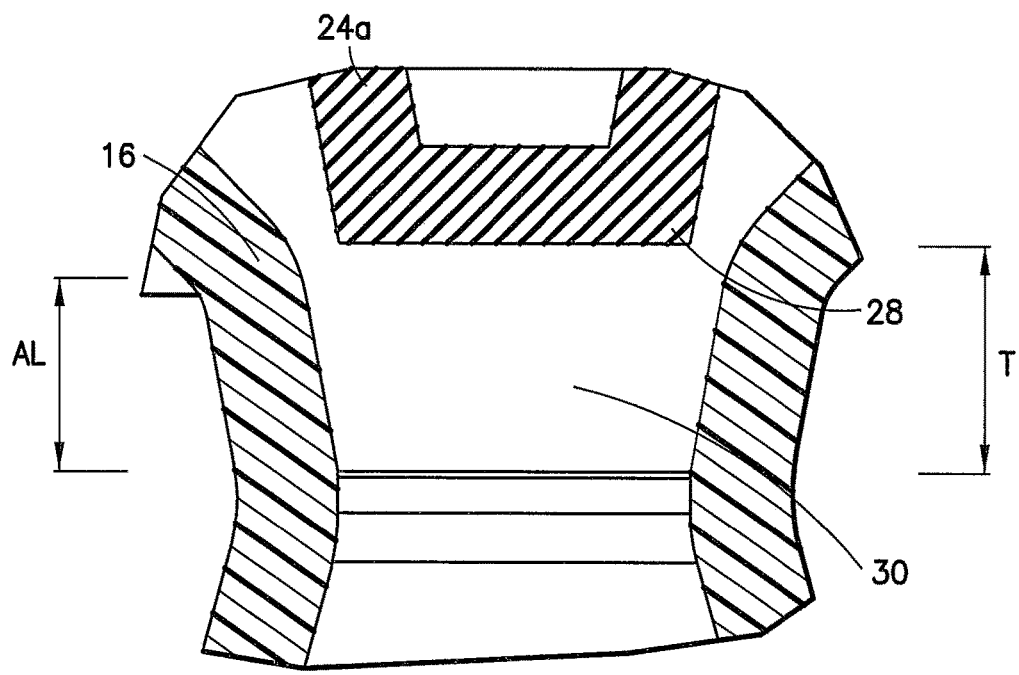
FIG. 6C is an exploded view of the valve/annulus interaction denoted by circle XI of FIG. 6A in accordance with an embodiment of the present invention.
Figure 6D:
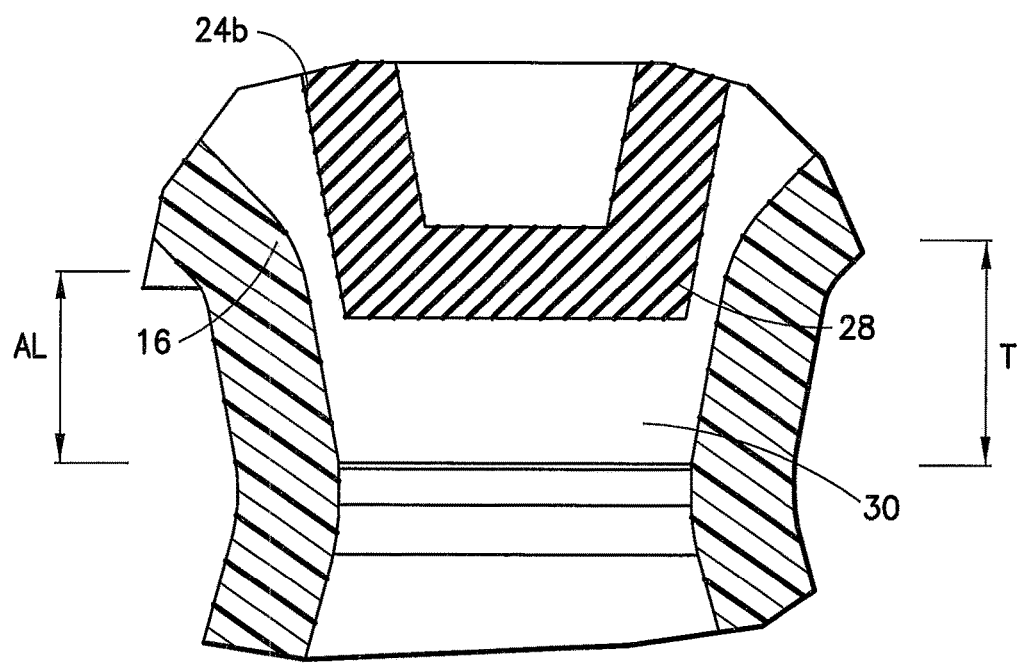
FIG. 6D is an exploded view of the valve/annulus interaction denoted by circle XII of FIG. 6B in accordance with an embodiment of the present invention.

With particular reference to FIGS. 1A, 1B, 2A, 2B, 6A, 6B, 6C, and 6D, in operation, when a blood collection tube 70 is attached to the blood collection device 40 as shown in FIG. 3, vacuum pressure is applied to the fluid transfer line "$P_{line}$" depicted as 16, in FIGS. 1A, 1C, and element 32 in FIG. 2B. During the initial stages of blood collection, this vacuum pressure can cause a large vacuum spike in the fluid transfer line "$P_{line}$" such that the vacuum pressure in the fluid transfer line "$P_{line}$" is less than pressure "$P_1$" in the regulator 10. Pressure "$P_1$" may be atmospheric pressure or positive pressure. Pressure "$P_1$" applies a force "F", as shown in FIG. 1C to the flexible member 22 causing the second end 28 of the valve 24 to enter into the orifice 30 of the housing outlet 16 to reduce the area, as shown by 35 in FIG. 1D, through which the blood can flow. FIGS. 6A and 6C-6D illustrate the movement "T" of the valve 24a-24b into the orifice 30 into the housing outlet 16. The orifice 30 has an annulus length "AL", as shown in FIGS. 6C-6D, into which the second end 28 of the valve 24 enters to restrict the flow of fluid through area 35. This smaller area 35 restricts and/or slows down the flow of blood through the housing outlet 16 and the rate at which the blood is withdrawn from the patient's blood vessel. After a predetermined amount of time, as the blood collection tube begins to fill, the force applied from the vacuum within the tube 70 decreases and the pressure in the fluid transfer line "$P_{line}$" equalizes to pressure "$P_1$" in the regulator 10 causing the flexible member 22 and valve 24 to withdraw from the orifice 30 of the housing outlet 16 to produce a larger area 35 in the orifice as shown in FIG. 1B and allow the blood to flow freely through the outlet and from the patient's blood vessel in an unrestricted manner.

It can be appreciated that while the drawings show restriction of the housing outlet 16, the blood flow direction can be reversed and in this reversed configuration, the valve 24 would be movable with respect to the housing inlet 14 to restrict the flow of blood entering into the housing 12 through the inlet 14.

The flexible member 22 can be a membrane formed from any type of flexible, resilient material such as a thermoplastic elastomer (TPE), silicone, and the like. The flexible member 22 can have spring-like properties which enable it to return to its at-rest position, as shown in FIGS. 1A and 2A. Referring back to FIG. 1 and with reference to FIGS. 5A and 5C, the flexible member 22 can be anchored about a perimeter 23 to a wall portion 19 of the wall 18 of the housing 12. A separate cap member 36 can be provided to assist in holding the flexible member 22. The flexible member 22 has a first face 22a directed to the housing interior 20 and a second face 22b directed toward the atmosphere. The flexible member 22 acts as a barrier between the blood "B" flowing through the housing 12 and the atmosphere. The valve 24 can be in the form of a needle valve having a tapered or conical shape. This valve 24 can be secured to the first face 22a of the flexible member 22 or can be integrally formed with the flexible member 22. The housing inlet 14 can be associated with a blood source, such as a patient's vein or artery, and the housing outlet 16 can be associated with a vacuum source, such as a vacuum blood collection tube 70, as discussed in detail above, and the pressure differential can be caused by the application of vacuum from the vacuum blood collection tube 70 to the housing outlet 16.

The regulator 10 is configured for integration with a blood collection device 40, such as a wingset as discussed above. The pressure regulator 10 can be directly associated with the hub 43 of the blood collection device 40. Alternatively, the pressure regulator 10 can be positioned at any location in-line with the tubing 44 or it can be directly associated with the collection holder 72. The pressure regulator 10 can include a thumb pad 34 associated with the flexible member 22 to enable the user to over-ride the automatic regulation of blood flow and to apply a downward force to move the valve 24 into the orifice 30 of the housing outlet 16 to manually regulate the flow of blood through the housing 12. According to an embodiment of the invention, as shown in FIGS.

7A-7D, a separate spring 37 and a plunger rod assembly including a thumb press 38 and plunger rod 39, may be associated with the atmospheric side or second face 22b of the flexible member 22.

FIGS. 8A-8C show partial cross-sectional views of a pressure regulator, generally indicated as 110, in accordance with another embodiment of the present invention. FIG. 8A shows an arrangement wherein the pressure in the fluid transfer line (not shown) is equal to atmospheric pressure allowing for unrestricted fluid flow, and FIG. 8C shows an arrangement wherein the pressure in the fluid transfer line $P_{line}$ is less than atmospheric pressure resulting in restricted fluid flow in accordance with an embodiment of the present invention. In this design, instead of a tapered needle valve 24, as shown in FIGS. 1A, 1C, 2A, 2C, 4, and 5A-5D, a valve 124 has a concentric annulus design, i.e., having a constant diameter along its longitudinal length. In this design, a first end 126 of the concentric annulus 124 is connected to a first face 122a of a flexible member 122. A second face 122b of the flexible member 122 is exposed to the pressure "$P_1$" of the regulator 110, which may be atmospheric or positive pressure. Upon the application of a differential or vacuum pressure, the pressure in the fluid transfer line "$P_{line}$" becomes less than atmospheric pressure causing the flexible member 122 to move into a housing 112 and causing a second end 128 of the concentric annulus 124 to move into an orifice 130 of a housing outlet 116. The pressure drop from the first end 126 of the concentric annulus 124 to the second end 128 is a function of the length "L1" (FIG. 8A) to L2 of the concentric annulus 124 (FIG. 8C). Therefore, when the pressure in a housing interior 120 is low, this low fluid pressure, along with atmospheric pressure applied to the second face 122b of the flexible member 122, causes the membrane 122 to be pulled down into the housing interior 120 and lengthen the concentric annulus 124, resulting in more fluid resistance, as shown by L2 in FIG. 8C and a slow down of the flow of blood "B" entering a housing inlet 114 and flowing through the housing 112 and out of the housing outlet 116. Optionally, a thumb pad (not shown) can be associated with the second face 122b of the flexible member 122 which can be manually depressed to override the automatic flexing of the flexible member 122 and to manually slow down the flow of blood "B" through the housing 112.

Reference is now made to FIG. 9 which is a cross-sectional view of a pressure regulator, generally indicated as 210, in accordance with another embodiment of the present invention. In this design, a flexible member 222 has a first face 222a that is secured to a first end 226 of a poppet type of valve 224. The flexible member 222 applies pressure to a poppet type of valve 224 upon the application of a differential pressure or vacuum within an interior 220 of a housing 212. The poppet valve 224 has a second end 228 that includes a flat shut-off 225 and an extension member 233 that is drawn toward an orifice 230 of a housing outlet 216 during the initial phase of the collection process when an evacuated tube 270 is inserted in a holder 272. This, in turn, slows down the withdrawal of blood "B" through a housing inlet 214, which is connected to a blood collection device 240. Optionally, a thumb pad 234 can be associated with the second face 222b of the flexible member 222. An opening 235 can be provided to enable the atmospheric pressure to enter therein and contact the flexible member 222. The thumb pad 234 can be manually depressed to override the automatic flexing of the flexible member 222 and apply a force to the poppet valve 224 to cause it to enter into the orifice 230 of the housing outlet 216 to manually slow down the flow of blood "B" through the housing 212.

Figure 10A:
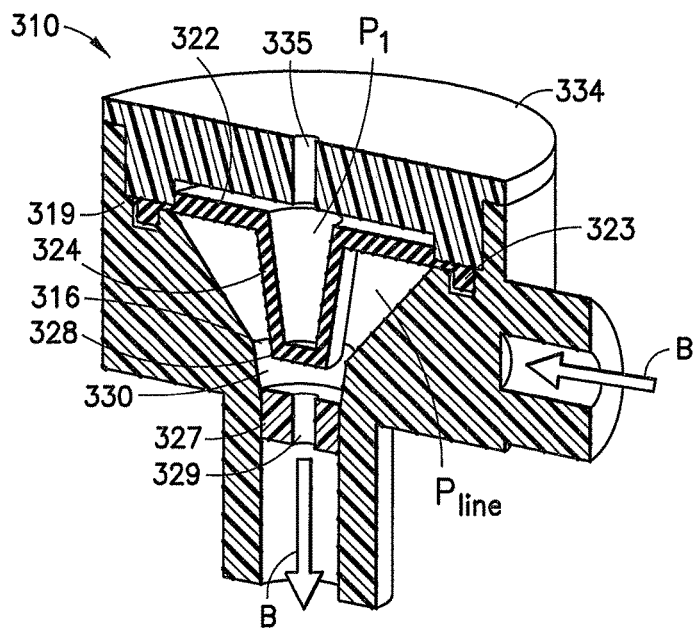
FIG. 10A is a cross-sectional front perspective view of a pressure regulator showing unrestricted fluid flow therethrough in accordance with yet another embodiment of the present invention.
Figure 10B:
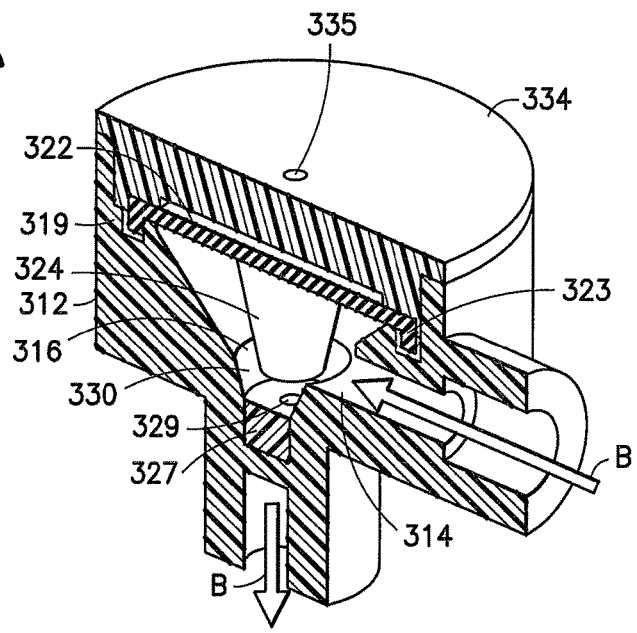
FIG. 10B is a cross-sectional side perspective view of the pressure regulator of FIG. 10A in accordance with an embodiment of the present invention.
Figure 11A:
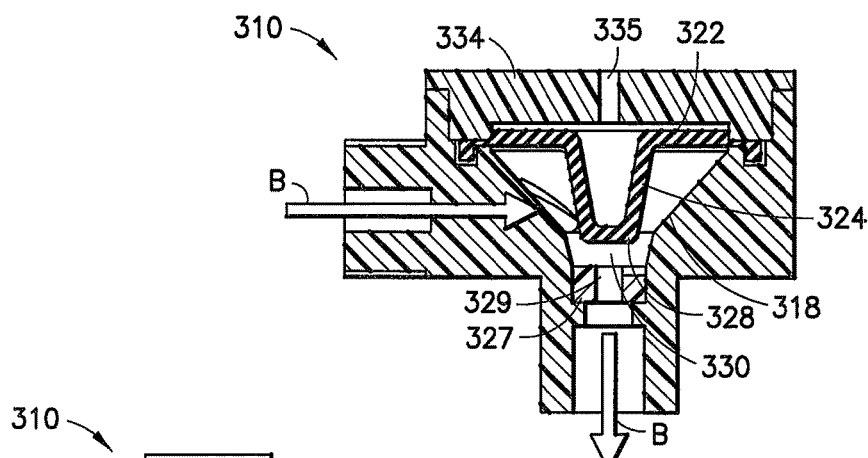
FIG. 11A is a left cross-sectional view of the pressure regulator of FIGS. 10A and 10B in accordance with an embodiment of the present invention.
Figure 11B:
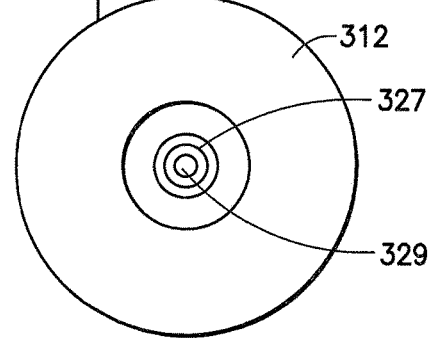
FIG. 11B is a bottom view of the pressure regulator of FIGS. 10A and 10B in accordance with an embodiment of the present invention.
Figure 11C:
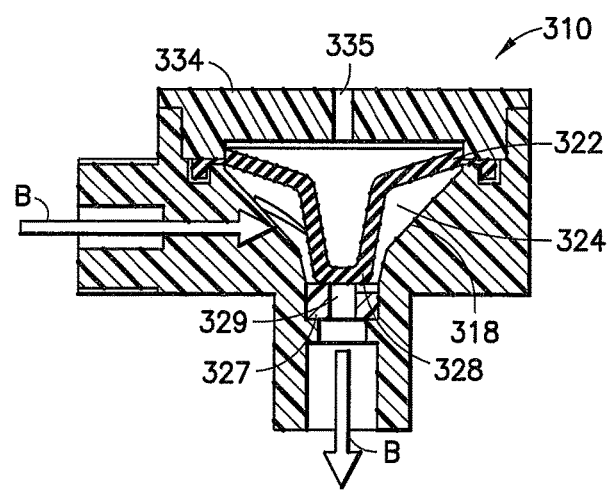
FIG. 11C is a left cross-sectional view of the pressure regulator of FIGS. 10A and 10B showing restricted/closed fluid flow therethrough in accordance with an embodiment of the present invention.
Figure 12A:
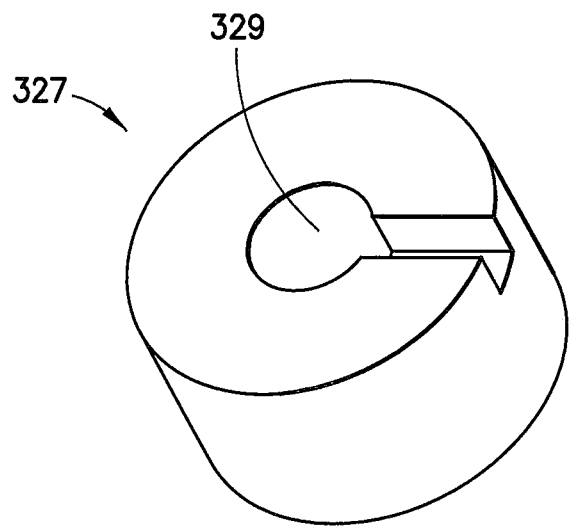
FIG. 12A is a top perspective view of the insert used in the regulator of FIGS. 10A and 10B in accordance with an embodiment of the present invention.
Figure 12B:
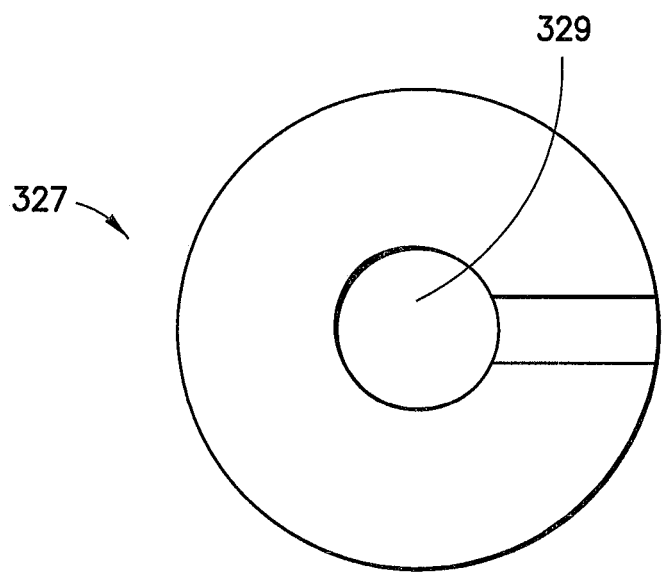
FIG. 12B is a top view of the insert used in the pressure regulator of FIGS. 10A and 10B in accordance with an embodiment of the present invention.

Referring now to FIGS. 10A-10B and 11A-11C there is shown a pressure regulator, generally indicated as 310, in accordance with yet another embodiment of the present invention. This pressure regulator 310 differs from the pressure regulators 10, 110, and 210, previously discussed in that the components of the device are laid out in a flow switch type of configuration. A seal ring 327, shown in detail in FIGS. 12A and 12B, is provided in an orifice 330 of a housing outlet 316, as shown in FIGS. 10A-10B. The seal ring 327 includes a small flow channel 329. A valve 324 can be integrally formed with a flexible member 322. The flexible member 322 can be mounted about its perimeter 323 to a wall portion 319 of a housing 312. The housing 312, shown in FIGS. 14A-14E, includes tapered sidewall portions 318 which are shaped to accommodate the valve portion 324 of flexible member 322 and define a housing interior 320. The housing outlet 316 includes orifice 330 configured to hold the seal ring 327. As illustrated in FIGS. 15A-15D, the flexible member 322 has a conical/tapered shape ending in a tip 328. Upon the exposure of the housing interior 320 of the housing 312 to a differential or vacuum pressure, this vacuum pressure in the fluid line "Pline" cooperates with the pressure "$P_1$" of the regulator 310 to cause the flexible member 322 and valve 324 to be drawn toward the seal ring 327, and the tip 328 cooperates with the seal ring 327 and small flow channel 329 to reduce or restrict the flow of blood "B" through the small flow channel 329. The geometry of the small flow channel 329 is set to add a prescribed amount of flow resistance to the fluid path "B". This resistance acts to decrease the flow rate through the blood collection device 40 of FIG. 3. The flexible member 322 can comprise a membrane possessing spring-like properties based upon its thickness, diameter, and mechanical properties, such as elasticity, that will cause the membrane to bias toward an unflexed position away from the seal ring 327 upon an equalization of pressure within the housing interior 320 wherein the downward force from the fluid pressure will be less than the upward force of the membrane. At this point, the membrane or flexible member 322 will release from the seal ring 327 and the additional resistance from the small flow channel 329 will be removed from the system. This will act to speed up the flow rate of the blood "B" toward the end of the blood collection process.

It can be appreciated that the pressure point where this release occurs can be designed into the pressure regulator 310 by the selection of the thickness, diameter, and mechanical properties of the flexible member 322. It can also be appreciated that the seal ring 327 could also be located in a housing inlet 314 and the pressure regulator 310 could be configured such that the flexible member 322 and valve 324 cooperate with the housing inlet 314.

Figure 13A:
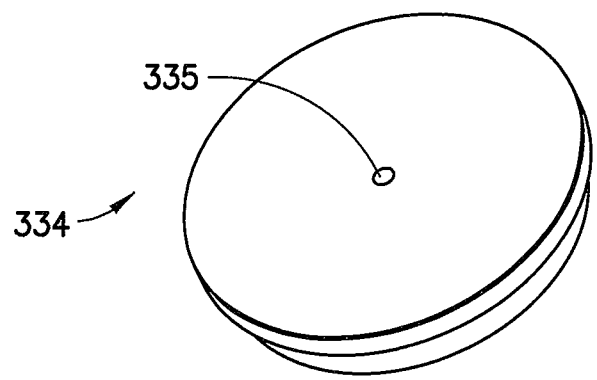
FIG. 13A is a top perspective view of the cap used in the pressure regulator of FIGS. 10A and 10B in accordance with an embodiment of the present invention.
Figure 13B:
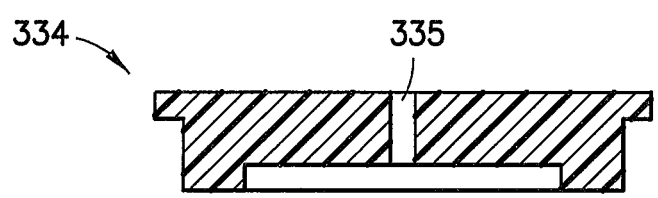
FIG. 13B is a cross-sectional side elevation view of the cap used in the pressure regulator of FIGS. 10A and 10B in accordance with an embodiment of the present invention.
Figure 14A:
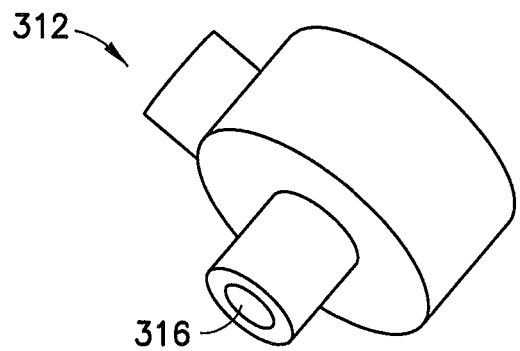
FIG. 14A is a top perspective view of the housing used in the pressure regulator of FIGS. 10A and 10B in accordance with an embodiment of the present invention.
Figure 14B:
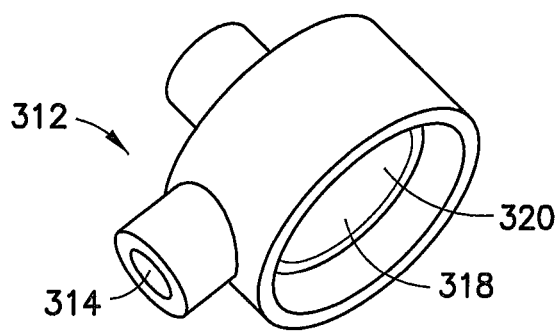
FIG. 14B is a bottom perspective view of the housing used in the pressure regulator of FIGS. 10A and 10B in accordance with an embodiment of the present invention.
Figure 14C:
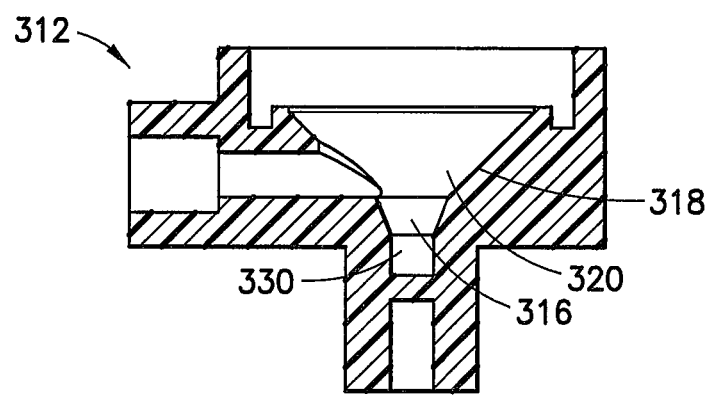
FIG. 14C is a left side view of the housing of FIGS. 14A and 14B in accordance with an embodiment of the present invention.
Figure 14D:
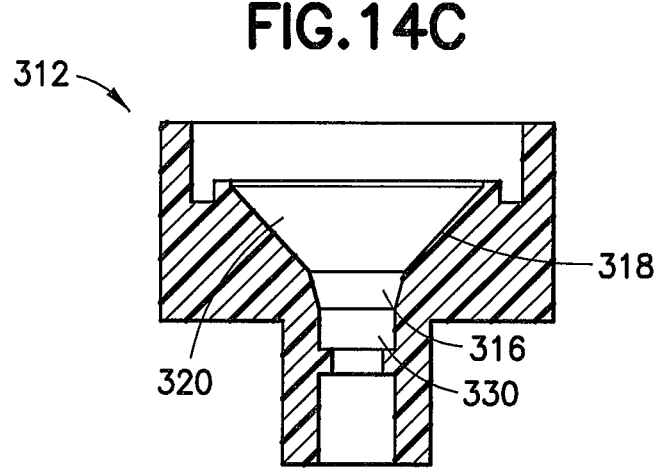
FIG. 14D is a rear cross-sectional view of the housing of FIGS. 14A and 14B in accordance with an embodiment of the present invention.
Figure 14E:
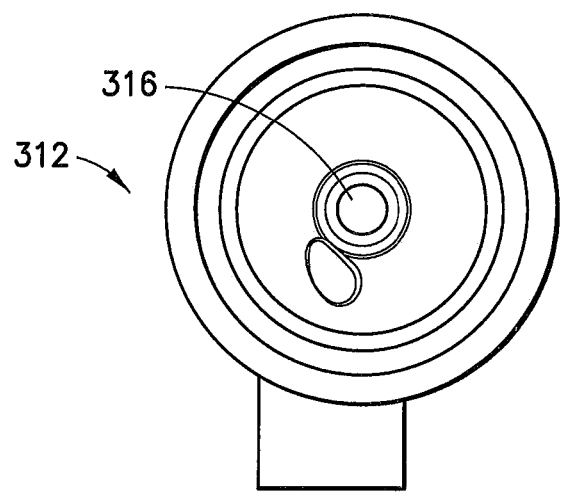
FIG. 14E is a top view of the housing used in the pressure regulator of FIGS. 14A and 14B in accordance with an embodiment of the present invention.

Optionally, a thumb pad 334, as shown in FIGS. 13A and 13B, can be associated with the flexible member 322. An opening 335 can be provided to enable the atmospheric pressure to enter therein and contact the flexible member 322. The thumb pad 334 can be manually depressed to over-ride the automatic flexing of the flexible member 322 and apply a force to the flexible member 322 to cause it to enter into the orifice 330 of the housing outlet 316 to manually slow down the flow of blood "B" through the housing 312.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of this description. For example, it is to be understood that the present invention contemplates that, to the extent possible, one or more features of any embodiment can be combined with one or more features of any other embodiment.

The invention claimed is:

1. A regulator for flow modulation during blood collection, said regulator comprising:
    a housing having a housing inlet, a housing outlet, and a wall defining a housing interior, at least a portion of said wall comprising a flexible member; and
    a valve associated with said flexible member, said valve in communication with said housing interior,
    wherein upon application of a differential pressure within the housing interior, at least one of the flexible member and valve are automatically movable with respect to either the housing inlet or housing outlet to modulate a flow of blood moving through the housing,
    wherein the housing outlet is associated with a vacuum source, and wherein the application of the differential pressure is initiated by the vacuum source,
    wherein the application of the differential pressure within the housing interior forces at least one of the flexible member and valve into an orifice of at least one of the housing inlet or housing outlet, thereby restricting the orifice and slowing a rate of a flow of blood passing through the housing, and
    wherein equalization of the pressure within the housing with an atmospheric pressure causes the flexible member or valve to at least partially withdraw from the orifice of the housing inlet or housing outlet, to allow the rate of the flow of blood passing through the housing to increase.

2. The regulator of claim 1 wherein the valve is movable with respect to the housing outlet to vary the geometry of an orifice of the housing outlet.

3. The regulator of claim 1 wherein the regulator is configured for integration with a blood collection wingset.

4. The regulator of claim 3 wherein said wingset comprises a hub, tubing, and a blood collection holder and wherein the regulator is directly associated with the hub, positioned in-line with the tubing, or is directly associated with the collection holder.

5. The regulator of claim 1 wherein the flexible member comprises a resilient membrane having spring properties that is anchored about its perimeter to the wall of the housing, and the valve is secured to the membrane.

6. The regulator of claim 1 including a thumb pad associated with the flexible member to enable a user to over-ride the automatic regulation of blood flow and to manually regulate the flow of blood through the housing.

7. The regulator of claim 1 wherein the valve comprises a needle valve.

8. The regulator of claim 1 wherein the valve comprises a poppet valve having a flat shut off.

9. The regulator of claim 1 including a spring associated with an atmospheric side of the flexible member and biased with the housing.

10. The regulator of claim 1 wherein the valve comprises a concentric annulus having an inner stein connected to the flexible member and wherein the application of a vacuum pressure within the housing causes the flexible member to be drawn into the housing interior to lengthen the concentric annulus.

11. The regulator of claim 10, wherein a dissipation of the vacuum pressure in the housing interior raises the flexible member with respect to the housing interior to decrease the length of the concentric annulus with respect to the housing inlet or housing outlet.

12. The regulator of claim 1 wherein the housing inlet or housing outlet includes a seal ring having a small flow channel and wherein the valve comprises the flexible member that is drawn toward the seal ring to cooperate with the seal ring and small flow channel to reduce or restrict the flow of blood through the small flow channel upon the application of a differential pressure within the housing interior.

13. The regulator of claim 12 wherein the flexible member comprises at least one spring element that causes a membrane to bias toward a position away from the seal ring upon an equalization of pressure within the housing interior.

* * * * *